United States Patent [19]

Maurer et al.

[11] Patent Number: 4,492,800
[45] Date of Patent: Jan. 8, 1985

[54] PROCESS FOR THE PREPARATION OF 1,1-DICHLORO-ALKENES

[75] Inventors: Fritz Maurer, Wuppertal; Uwe Priesnitz, Solingen; Hans-Jochem Riebel, Wuppertal, all of Fed. Rep. of Germany

[73] Assignee: Bayer Aktiengesellschaft, Leverkusen, Fed. Rep. of Germany

[21] Appl. No.: 468,786

[22] Filed: Feb. 22, 1983

Related U.S. Application Data

[63] Continuation of Ser. No. 237,006, Feb. 23, 1981, abandoned.

[30] Foreign Application Priority Data

Mar. 12, 1980 [DE] Fed. Rep. of Germany ....... 3009485

[51] Int. Cl.³ .................. C07C 69/74; C07C 121/48; C07C 121/60
[52] U.S. Cl. .................. 562/506; 260/464; 260/465 D; 560/8; 560/101; 560/124; 562/405; 562/491; 564/161; 564/181; 564/190; 568/316; 568/348; 570/217
[58] Field of Search ............ 568/347, 348, 316; 260/464, 465 D; 564/190, 181, 161; 560/124, 8, 101; 562/506, 405, 491

[56] References Cited

FOREIGN PATENT DOCUMENTS 2849 7/1979 European Pat. Off. .

OTHER PUBLICATIONS

Fieser, et al., Reagents for Organic Synthesis, vol. 4, (1974), p. 315; vol. 6, (1977), p. 351.
Patai, The Chemistry of the Carbonyl Group, (1966), pp. 570–571.

*Primary Examiner*—Joseph Paul Brust
*Attorney, Agent, or Firm*—Sprung, Horn, Kramer & Woods

[57] ABSTRACT

A process for the preparation of a 1,1-dichloro-alkene of the formula

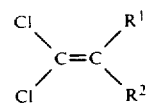

in which
R¹ is hydrogen, or an optionally substituted alkyl, alkenyl, alkinyl, cycloalkyl, aralkyl, aralkenyl or aryl radical, and
R² is an optionally substituted alkyl, alkenyl, alkinyl, cycloalkyl, aralkyl, aralkenyl or aryl radical, or
R¹ and R² together form an optionally branched and/or optionally benzo-fused hydrocarbon chain, comprising reacting a carbonyl compound of the formula

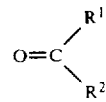

with a trichloromethanephosphonic acid ester of the formula

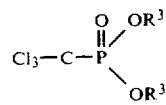

in which
R³ each individually is an alkyl or phenyl radical, or together are alkanediyl, in the presence of at least an equimolar amount of magnesium. Advantageously,
R¹ is hydrogen,
R² is a $C_2$ to $C_5$ alkenyl radical or a radical of the formula

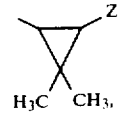

Z is a cyano, acetal, carboxyl or $C_1$ to $C_4$ alkoxycarbonyl radical, or a radical of the formula COOM, and
M is sodium or potassium,
R³ each individually is a $C_1$ to $C_4$ alkyl or phenyl radical, or the two radicals R³ together are $C_2$ to $C_5$ alkanediyl, about 0.95 to 1.4 moles of the trichloromethanephosphonic acid ester and about 1.5 to 4 moles of magnesium are employed per mole of the carbonyl compound, and the reaction is carried out at a temperature between about 0° and 150° C. in a polar aprotic solvent. The products are known intermediates, especially for insecticides.

6 Claims, No Drawings

PROCESS FOR THE PREPARATION OF 1,1-DICHLORO-ALKENES

This is a continuation of application Ser. No. 237,006 filed Feb. 23, 1981, now abandoned.

The invention relates to an unobvious process for the preparation of certain 1,1-dichloroalkenes.

It is known that 1,1-dichloro-alkenes are obtained when lithium salts of dichloromethanephosphonic acid esters are reacted with aldehydes or ketones (see Synthesis 1975, 458–461 and 535–536). The preparation of the lithium salts of dichloromethanephosphonic acid esters is, however, troublesome. They are obtained from chloromethanephosphonic acid esters or trichloromethanephosphonic acid esters by reaction with butyl-lithium and, if appropriate, carbon tetrachloride at −70° to −80° C., it being necessary to use carefully dried solvents, and an inert gas atmosphere being required.

The present invention now provides a process for the preparation of 1,1-dichloro-alkenes of the general formula

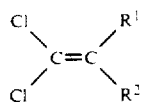

in which
R¹ represents a hydrogen atom or an optionally substituted alkyl, alkenyl, alkinyl, cycloalkyl, aralkyl, aralkenyl or aryl radical and R² represents an optionally substituted alkyl, alkenyl, alkinyl, cycloalkyl, aralkyl, aralkenyl or aryl radical,
or in which
the two radicals R¹ and R² together represent an optionally branched and/or optionally benzofused hydrocarbon chain,
in which a carbonyl compound of the general formula

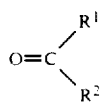

in which
R¹ and R² have the above mentioned meaning,
is reacted with a trichloromethanephosphonic acid ester of the general formula

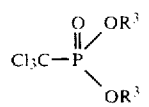

in which
the two radicals R³ individually represent an alkyl or phenyl radical, or
the two radicals R³ together represent alkanediyl (alkylene),
in the presence of at least the equimolar amount of magnesium and optionally in the presence of a diluent, and optionally at a temperature between 0° and 150° C.

It is surprising that 1-1-dichloroalkenes of the formula (I) are obtained in good yields in a considerably simpler and less expensive manner by the process according to the invention than could be expected in view of the state of the art.

If, for example, 3-formyl-2,2-dimethyl-cyclopropane-1-carboxylic acid methyl ester, trichloromethanephosphonic acid dimethyl ester and magnesium are used as starting substances, the reaction according to the present invention is illustrated by the following equation:

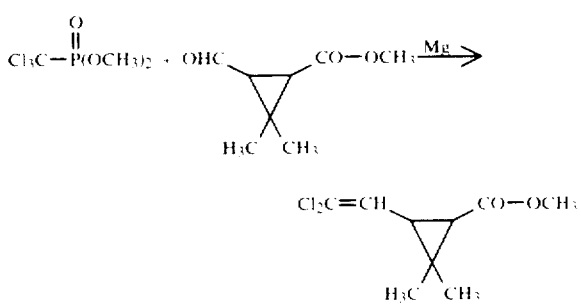

Preferred carbonyl compounds of formula (II) to be used as starting substances are those in which
R¹ represents a hydrogen atom, an optionally halogen-substituted $C_1$ to $C_5$ alkyl radical, an optionally halogen-substituted benzyl or phenylethyl radical, or a phenyl radical which is optionally substituted by halogen, $C_1$ to $C_4$ alkoxy, methylenedioxy, cyano and/or nitro and
R² represents an optionally halogen-substituted $C_1$ to $C_5$ alkyl radical, a $C_2$ to $C_5$ alkenyl or $C_2$ to $C_5$ alkinyl radical, an optionally halogen-substituted benzyl or phenylethyl radical, a phenyl radical which is optionally substituted by halogen, $C_1$ to $C_4$ alkyl, $C_1$ to $C_4$ alkoxy, methylenedioxy, cyano and/or nitro, an optionally halogen-substituted styryl radical or a radical of the general formula

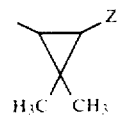

wherein
Z represents an acetyl, cyano, carbamoyl or $C_1$ to $C_4$ alkoxycarbonyl radical or a radical of the formula COOM,
wherein
M represents a hydrogen atom, an alkali metal, one equivalent of an alkaline earth metal or an ammonium radical.

Particularly preferred starting substances are those compounds of the formula (II)
in which
R¹ represents a hydrogen atom and
R² represents a $C_2$ to $C_5$ alkenyl radical or a radical of the general formula

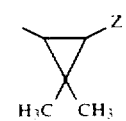

wherein

Z represents a cyano, acetyl, carboxyl or $C_1$ to $C_4$ alkoxycarbonyl radical or a radical of the formula COOM, wherein M represents sodium or potassium.

Examples of starting compounds of the formula (II) which may be mentioned are: β,β-dimethyl-acrolein, 3-formyl-2,2-dimethyl-1-cyano-cyclopropane, 3-formyl-2,2-dimethyl-1-acetyl-cyclopropane, 3-formyl-2,2-dimethyl-cyclopropane-1-carboxylic acid and its sodium salt, and 3-formyl-2,2-dimethyl-cyclopropane-1-carboxylic acid methyl ester, ethyl ester, n-propyl ester, iso-propyl ester, n-butyl ester, iso-butyl ester, sec.-butyl ester and tert.-butyl ester.

Compounds of the formula (II) are known (see Synthesis 1975, 535–536; and Tetrahedron Lett. 1976, 1979–1982). One synthesis route is outlined in the following equation (in which R represents a $C_1$ to $C_4$ alkyl radical):

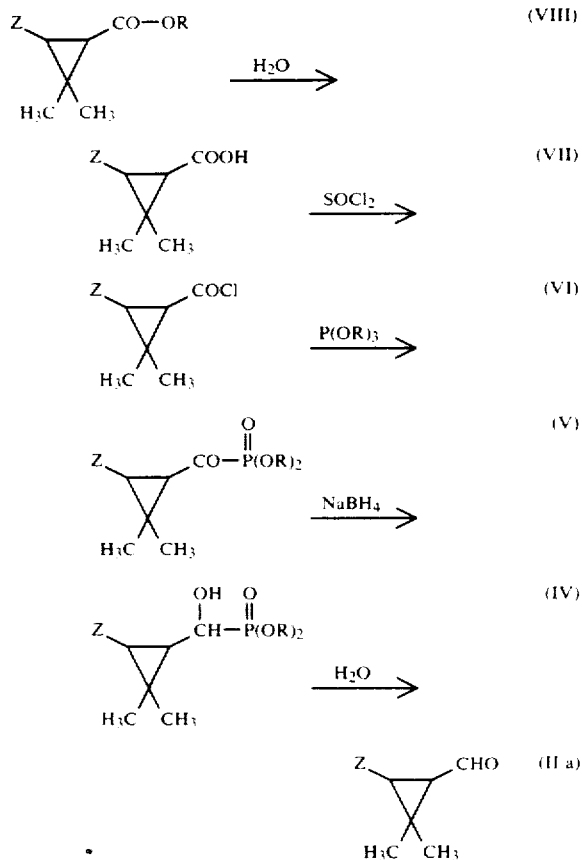

Hydrolysis of known cyclopropanecarboxylic acid esters of the formula (VIII) (see J.Org.Chem. 32 (1967), 3351–3355; Bull.Soc.Chim.Belg. 87 (1978), 721–732; and Tetrahedron Lett. 1978, 1847–1850), for example by reactionn with aqueous-alcoholic potassium hydroxide solution at temperatures between 20° and 100° C. and subsequent acidification, gives the carboxylic acids of the formula (VII). These can be converted into the acid chlorides of the formula (VI) by reaction with halogenating agents, for example thionyl chloride, at temperatures between 20° and 80° C.

Reaction of the acid chloride (VI) with trialkyl phosphites at temperatures between −20° and +150° C., preferably between 0° and 120° C., gives the cyclopropanoylphosphonic acid esters of the formula (V) (see J.Am.Chem.Soc. 86 (1964), 3862–3866; and Methoden der organischen Chemie (Methods of Organic Chemistry) (Houben-Weyl-Müller), 4th edition, Volume 12/1, page 453, Georg-Thieme-Verlag, Stuttgart 1963). The products are isolated and purified, if appropriate, by distillation under reduced pressure.

The α-hydroxy-phosphonic acid esters of the formula (IV) are obtained by reducing the oxo compounds of the formula (V) with sodium tetrahydridoborate, if appropriate using a diluent, for example water or aqueous methanol, at temperatures between −20° and +50° C., the pH value being kept between 5 and 8 by addingg a buffer agent, for example sodium hydrogen phosphate (see Chem.Ber. 103 (1970), 2984–2986). For working up, the mixture is extracted with a water-immiscible solvent, for example methylene chloride, the extracts are dried and filtered and the solvent is distilled off from the filtrate under reduced pressure.

The corresponding aldehydes of the formula (II a) can be prepared from the α-hydroxy-phosphonic acid esters of the formula (IV) by treatment with sodium hydroxide solution at temperatures between 0° and 100° C., preferably between 10° and 50° C. (see Chem.Ber. 103 (1970), 2984–2986).

As an alternative to the preparation process outlined above, aldehydes of the formula (II a) are also obtained by reacting acid chlorides of the formula (VI) with lithium tri-tert.-butoxy-hydrido-aluminate, which, if appropriate, has been prepared in situ from lithium tetrahydroaluminate and tert.-butanol, the reaction being carried out, if appropriate, in the presence of a diluent for example, tetrahydrofurane, at temperatures beween −100° and +100° C., preferably between −80° and +50° C. For working up, the mixture is poured into a mixture of hydrochloric acid and ice-water and extracted with a water-immiscible solvent, for example diethyl ether. The extracts are dried, filtered and concentrated. The crude product is purified, if appropriate, by distillation.

Preferred trichloromethanephosphonic acid esters formula (III) also to be used as starting substances are those in which the radicals $R^3$ individually represent a $C_1$ to $C_4$ alkyl or phenyl radical or the two radicals $R^3$ together represent $C_2$ to $C_5$ alkanediyl.

Examples which may be mentioned are trichloromethanephosphonicacid dimethyl ester, diethyl ester, dipropyl ester and diphenyl ester.

Compounds of the formula (III) are known (see J.Am.Chem.Soc. 69 (1947), 1002; and ibid. 77 (1955), 1156).

The process according to the invention is preferably carried out using diluents. Possible diluents are virtually any of the inert organic solvents, in particular aprotic polar solvents. These include ethers (for example glycol dimethyl ether, diglycol dimethyl ether, tetrahydrofuran and dioxane), carboxylic acid amides (for example dimethylformamide, dimethylacetamide and N-methylpyrrolidone), sulphoxides (for example dimethylsulphoxide), phosphoric acid amides (for example hexamethylphosphoric acid triamide), and nitriles (for example acetonitrile and propionitrile).

The reaction temperature can be varied within a substantial range. In general, the reaction is carried out between 0° and 150° C., preferably at 10° to 80° C.

The process according to the invention is in general carried out under normal pressure.

0.9 to 1.2 moles, preferably 0.95 to 1.1 moles, of trichloromethanephosphonic acid ester of the formula (III) and 1 to 5 moles, preferably 1.5 to 4 moles, of magnesium are generally employed per mole of carbonyl compound of the formula (II).

For carrying out the process according to the invention, the magnesium is preferably initially introduced, in a diluent, into the reaction vessel and the starting substances of the formulae (II) and (III) are simultanously added dropwise. The reaction mixture is stirred until the reaction has ended and is then filtered.

Working up can be carried out by customary methods, for example by a procedure in which the filtrate is diluted with water and extracted with an organic solvent which is virtually immiscible with water, for example methylene chloride, the organic phase is dried and filtered and the filtrate is evaporated. The products, which remain in the residue, can be purified in the customary manner, for example by vacuum distillation.

Some of the 1,1-dichloro-alkenes which can be prepared by the process according to the invention can be used as intermediate products for the preparation of insecticidally and acaricidally active pyrethroids (see DE-OS (German Published Specification) 2,326,977).

PREPARATIVE EXAMPLES

Example 1

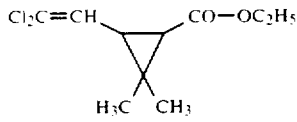

A mixture of 25.5 g (0.1 mole) of trichloromethanephosphonic acid diethyl ester and 17.2 g (0.1 mole) of 3-formyl-2,2-dimethyl-cyclopropane-1-carboxylic acid ethyl ester was added dropwise to 9.6 g of activated magnesium filings in 100 ml of dimethylformamide in a manner such that the reaction temperature did not exceed 60° C. When the exothermic reaction had ended, the reaction mixture was allowed to cool to room temperature. It was then filtered. 200 ml of water were added to the filtrate; this solution was extracted twice with 100 ml of methylene chloride each time. The combined methylene chloride extracts were dried over sodium sulphate and filtered. The filtrate was distilled. 3-(2,2-Dichloro-vinyl)-2,2-dimethyl-cyclopropane-1-carboxylic acid ethyl ester was obtained in a yield of 60% of theory.

The structure was proved by comparative gas chromatography and by nuclear magnetic resonance spectroscopy.

EXAMPLE 2

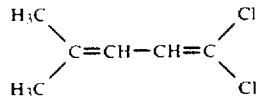

2.4 g of activated magnesium filings were suspended in 50 ml of dimethylformamide, and a mixture of 12.8 g (0.05 mole) of trichloromethanephosphonic acid diethyl ester and 4.2 g (0.05 mole) of β,β-dimethylacrolein was added. The temperature rose to about 45° C. The mixture was stirred at 60° to 70° C. for 1 hour, 300 ml of water was added and the mixture was extracted 3 times with 50 ml of n-hexane each time. The organic extracts were dried over sodium sulphate and evaporated in vacuo. The residue was distilled in vacuo. 5.2 g (69% of theory) of 1,1-dichloro-3,3-dimethylbutadiene were thus obtained in the form of a colorless liquid with a boiling point of 53° to 55° C./10 mm Hg.

It will be understood that the specification and examples are illustrative but not limitative of the present invention and that other embodiments within the spirit and scope of the invention will suggest themselves to those skilled in the art.

We claim:

1. A process for the preparation of a 1,1-dichloroalkene of the formula

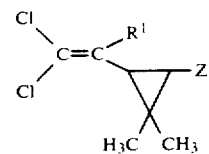

in which
R$^1$ is hydrogen, or an alkyl, alkenyl or alkinyl radical with up to 5 carbon atoms, or a cycloalkyl, phenalkyl, phenalkenyl, or phenyl radical,
Z is an acetyl, cyano, carbamoyl or C$_1$ to C$_4$ alkoxycarbonyl radical, or a radical of the formula COOM, and
M is a hydrogen atom, an alkali metal, one equivalent of an alkaline earth metal or an ammonium radical,
consisting essentially of reacting a carbonyl compound of the formula

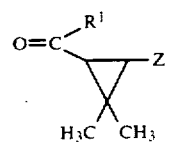

with a trichloromethanephosphonic acid ester of the formula

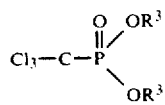

in which
R$^3$ each individually is a C$_1$ to C$_4$ alkyl or phenyl radical, or
together are C$_2$ to C$_5$ alkanediyl,
in the presence of at least an equimolar amount of elemental magnesium metal based on the carbonyl compound at a temperature between about 0° and 150° C.

2. A process according to claim 1, in which
R$^1$ is hydrogen,
Z is COOM
M is sodium or potassium.

3. A process according to claim 1, in which the reaction is carried out in an inert organic solvent.

4. A process according to claim 3, in which the solvent is a polar aprotic solvent.

5. A process according to claim 1, in which about 0.9 to 1.2 moles of the trichloromethanephosphonic acid ester and about 1.5 to 4 moles of magnesium are employed per mole of the carbonyl compound.

6. A process according to claim 2, in which about 0.95 to 1.4 moles of the trichloromethanephosphonic acid ester and about 1.5 to 4 moles of magnesium are employed per mole of the carbonyl compound, and the reaction is carried out at a temperature between about 0° and 150° in a polar aprotic solvent.

UNITED STATES PATENT AND TRADEMARK OFFICE
CERTIFICATE OF CORRECTION

PATENT NO. : 4,492,800
DATED : January 8, 1985
INVENTOR(S) : Fritz Maurer, et al It is certified that error appears in the above-identified patent and that said Letters Patent is hereby corrected as shown below:

Col. 2, line 29       After "halogen," insert --$C_1$ to $C_4$ alkyl,--

Col. 3, line 59       Correct spelling of "reaction"
Col. 3, line 66       Correct "chlorides"
Col. 4, line 13       Correct spelling of "adding"
Col. 5, line 11       Correct spelling of "simultaneously"

Signed and Sealed this

Twenty-eighth Day of May 1985

[SEAL]

Attest:

DONALD J. QUIGG

Attesting Officer       Acting Commissioner of Patents and Trademarks